US012193830B2

(12) United States Patent
Egorov

(10) Patent No.: US 12,193,830 B2
(45) Date of Patent: Jan. 14, 2025

(54) METHOD FOR CHARACTERIZATION OF THE FEMALE PELVIC FLOOR WITH A BIOMECHANICAL INTEGRITY SCORE

(71) Applicant: Vladimir Egorov, Princeton, NJ (US)

(72) Inventor: Vladimir Egorov, Princeton, NJ (US)

(73) Assignee: Advanced Tactile Imaging Inc., Ewing, NJ (US)

( * ) Notice: Subject to any disclaimer, the term of this patent is extended or adjusted under 35 U.S.C. 154(b) by 663 days.

(21) Appl. No.: 17/526,271

(22) Filed: Nov. 15, 2021

(65) Prior Publication Data

US 2022/0087595 A1  Mar. 24, 2022

Related U.S. Application Data

(63) Continuation-in-part of application No. 17/028,636, filed on Sep. 22, 2020, now abandoned.

(51) Int. Cl.
*A61B 5/00* (2006.01)
(52) U.S. Cl.
CPC .......... *A61B 5/4337* (2013.01); *A61B 5/0053* (2013.01); *A61B 5/4884* (2013.01)
(58) Field of Classification Search
CPC ... A61B 5/0048; A61B 5/0053; A61B 5/4337; A61B 5/4884; A61B 8/08; A61B 8/12; A61B 8/4416; A61B 8/445; A61B 8/485; A61B 8/5223; A61B 8/5246
See application file for complete search history.

(56) References Cited

U.S. PATENT DOCUMENTS

| 8,052,622 | B2 | 12/2011 | Egorov | |
|---|---|---|---|---|
| 8,187,208 | B2 | 5/2012 | Egorov | |
| 8,419,659 | B2 | 4/2013 | Egorov | |
| 8,840,571 | B2 | 9/2014 | Egorov | |
| 2002/0143275 | A1 | 10/2002 | Sarvazyan | |
| 2002/0156370 | A1 | 10/2002 | Desouza | |
| 2008/0128626 | A1* | 6/2008 | Rousso | A61B 6/4258 250/362 |
| 2008/0139921 | A1 | 6/2008 | Biglieri | |
| 2013/0144191 | A1 | 2/2013 | Egorov | |
| 2014/0275841 | A1 | 9/2014 | Borazjani | |
| 2020/0037950 | A1* | 2/2020 | Egorov | A61B 5/6867 |

OTHER PUBLICATIONS

Egorov V, van Raalte H, Lucente V, Sarvazyan A. Biomechanical characterization of the pelvic floor using tactile imaging. Chapter 16 in Biomechanics of the Female Pelvic Floor, Elsevier, p. 317-348, 2016.

* cited by examiner

*Primary Examiner* — Shahdeep Mohammed
(74) *Attorney, Agent, or Firm* — Boris Leschinsky

(57) ABSTRACT

The Biomechanical Integrity Score and its five components are calculated as a result of vaginal tactile probe insertion, elevation, rotation, Valsalva maneuver, voluntary pelvic muscle contraction, reflex contraction, and relaxation while the probe is in contact with vaginal walls for a comprehensive biomechanical characterization of the pelvic floor. The probe is equipped with a plurality of tactile sensors recording various static and dynamic pressure patterns during a vaginal examination.

16 Claims, 10 Drawing Sheets

METHOD FOR CHARACTERIZATION OF THE FEMALE PELVIC FLOOR WITH A BIOMECHANICAL INTEGRITY SCORE

CROSS-REFERENCE TO RELATED APPLICATIONS

This U.S. patent application is a continuation-in-part of the U.S. patent application Ser. No. 17/028,636 filled Sep. 22, 2020, by the same inventor with the title "METHODS FOR VAGINAL TACTILE AND ULTRASOUND IMAGE FUSION", which in turn is a continuation-in-part of the U.S. patent application Ser. No. 15/249,672 filled Aug. 29, 2016, by the same inventor with the title "METHODS AND PROBES FOR VAGINAL TACTILE AND ULTRASOUND IMAGING", now abandoned, which claims a priority benefit from the U.S. Provisional Patent Application No. 62/215,227 filed Sep. 8, 2015, by the same inventor with the same title. The Ser. No. 17/028,636 patent application is also a continuation-in-part of the U.S. patent application Ser. No. 16/055,265 filled Aug. 6, 2018, by the same inventor with the title "METHODS FOR BIOMECHANICAL MAPPING OF THE FEMALE PELVIC FLOOR", now abandoned. The Ser. No. 17/028,636 patent application further claimed a priority date benefit of the U.S. Provisional Patent Application No. 62/706,663 filed Sep. 2, 2020, by the same inventor with the title "METHODS FOR VAGINAL TACTILE AND ULTRASOUND IMAGE FUSION". All of the above documents are incorporated herein in their respective entireties by reference.

GOVERNMENT-SPONSORED RESEARCH

This invention was made with the US Government support under grant number AG034714 awarded by the National Institute on Aging and grant number HD097805 awarded by National Institute of Child Health & Human Development, National Institutes of Health, and under contract number W81XWH1920018 awarded by the U.S. Army Medical Research Acquisition Activity, Department of Defense. The US Government has certain rights in this invention.

FIELD OF THE INVENTION

The present invention generally relates to female pelvic floor imaging. Specifically, the invention describes methods and devices for providing vaginal tactile imaging to characterize the biomechanical and functional conditions of the female pelvic floor.

BACKGROUND

Pelvic organ prolapse (POP) is an abnormal descent or herniation of the pelvic organs from their normal attachment sites or their normal position in the pelvis. This condition is often associated with concomitant pelvic floor disorders, including urinary and fecal incontinence, pelvic pain, sexual dysfunction, voiding dysfunction, and social isolation. A recent study provided a projection that by the year 2050, 43.8 million women, or nearly 33% of the adult female population in the US, would be affected by at least one troublesome pelvic floor disorder. The lifetime risk of undergoing surgery for POP or urinary incontinence is near 20%.

Urinary incontinence (UI) is a storage symptom and defined as the complaint of any involuntary loss of urine. The most common type of UI is stress urinary incontinence (SUI), defined as the complaint of involuntary leakage on effort or exertion, or on sneezing or coughing. Estimates of the prevalence of this disorder vary depending on the affected population and the definition of UI. Using the inclusive definition of any leakage occurring at least once, in the past year, the prevalence of UI ranges from 25% to 51%.

The female pelvic floor comprises the pelvic diaphragm muscles (pubococcygeus, puborectalis, and iliococcygeus, together known as the levator ani), the urogenital diaphragm muscles (ischiocavernosus, bulbospongiosus, and transverses perinei superficialis, together known as the perineal muscles); and the urethral and anal sphincter muscles. These muscles interrelate with each other both anatomically and functionally. The normal action of the pelvic floor muscles has been described as a squeeze around the pelvic openings and an inward lift. The pelvic floor disorders result from the neuro-urinary pathology as well as muscle functional impairment due to changes in biomechanical properties of soft tissues associated with age. The anatomy of the pelvic floor is complex and clinical examination alone is often insufficient to diagnose and assess the pathology. That is why a quantitative pelvic floor characterization and diagnosis must include biomechanical measurements. The need exists to improve the characterization of pelvic conditions.

The current clinical practice for the assessment of pelvic floor disorders is often limited to the evaluation of surface anatomy and manual palpation. Pelvic Organ Prolapse Quantification system (POP-Q) is widely used for describing and staging pelvic support [Bump, R. C., Mattiasson, A., Bo, K., et al. The Standardization of Terminology of Female Pelvic Organ Prolapse and Pelvic Floor Dysfunction. *American Journal of Obstetrics and Gynecology* 1996; 175: 10-17], the Pelvic Floor Distress Inventory (PFDI) and PFDI-20 are recommended by the International Consultation on Incontinence as grade A for assessing pelvic floor dysfunction [de Arruda G T, Dos Santos Henrique T, Virtuoso J F. Pelvic floor distress inventory (PFDI)-systematic review of measurement properties. *Int Urogynecol J.* 2021; 32(10): 2657-2669.], the Female Sexual Function Index (FSFI) is used for diagnosing sexual dysfunction in women [Okobi O E. A Systemic Review on the Association Between Infertility and Sexual Dysfunction Among Women Utilizing Female Sexual Function Index as a Measuring Tool. *Cureus* 2021; 13(6): e16006.]. In severe or complicated cases, ultrasound, magnetic resonance imaging (MRI), and X-ray imaging may be used for additional evaluation. Bladder and rectum function tests, such as urodynamics, manometry, or defecography might also be employed. No quantitative biomechanical indexes exist for the assessment of the female pelvic floor conditions.

The true etiology of POP and variations observed among individuals are not entirely understood. The pelvic disorders are thought to share common pathogeneses, tissue elasticity changes, weakening of the connective support tissues, and pelvic muscle dysfunction. Logically to propose that a biomechanical assessment and characterization of the female pelvic floor could bring important information in clinical practice. However, ultrasound and MRI elastography, as well as functional imaging of the pelvic floor, did not get appropriate acceptance in Urogynecology. There is a significant gap in biomechanical and functional research of the female pelvic floor.

Treatment options for POP and SUI include surgery and pelvic muscle training. An invasive surgical approach is considered the ultimate treatment for both POP and SUI. It was found that surgical treatments of recurrent SUI are associated with high failure rates. Physical training and medications are often not effective. There is a need for the objective and quantitative pre- and post-surgery assessment of pelvic floor conditions to improve evidence-based management in urogynecological surgeries.

The Vaginal Tactile Imager (VTI) was developed to provide a biomechanical mapping of the pelvic floor with a vaginal probe. A set of new clinical markers/parameters has been proposed for the biomechanical characterization of the pelvic floor conditions [Egorov, V. Methods for biomechanical mapping of the female pelvic floor. U.S. patent application Ser. No. 16/055,265 filled Aug. 6, 2018]. This set included 52 parameters automatically calculated in results of the completion of eight examination procedures (tests). However, this approach did not gain momentum among urogynecologists. The reasons for that are the long list of parameters and difficulties in their explanations to clinicians and patients. To make a biomechanical mapping in urogynecology more accessible and useful, further work is required on developing a shorter list of easily understandable and practical parameters, There is a need for a single new integral parameter for the characterization of the female pelvic floor conditions.

SUMMARY

The object of the present invention is to overcome the drawbacks of the prior art and to provide novel methods for objective and comprehensive characterization of the female pelvic floor.

Another object of the invention is to provide novel methods for objective characterization with an integral biomechanical parameter.

Another object of the invention is to provide novel methods for objective characterization with a limited number of components with different biomechanical aspects contributing to the integral biomechanical parameter.

Another object of the invention is to provide novel methods for objective characterization with the integral biomechanical parameter sensitive to POP development.

Another object of the invention is to provide novel methods for characterizing pelvic floor tissues and muscles as biomechanical elements based on tissue strain-stress and muscle functional data.

According to the present invention, novel methods for characterization of female pelvic floor via vaginal tactile and ultrasound image fusion may include the following steps:
  a) recording tactile response for vaginal walls in contact with the vaginal tactile imaging probe during vaginal wall deformation caused by moving the vaginal tactile imaging probe;
  b) recording dynamic pressure patterns on vaginal walls in contact with the vaginal tactile imaging probe during voluntary and reflex pelvic muscle contractions and involuntary relaxation and Valsalva maneuver and without further movement of the vaginal tactile imaging probe;
  c) using the recorded tactile responses in step (b) and the recorded dynamic pressure patterns in step (c) for calculating a set of biomechanical components to characterize each of:
    i. vaginal tissue elasticity,
    ii. pelvic support strength,
    iii. pelvic muscle contraction,
    iv. pelvic muscle involuntary relaxation,
    v. pelvic muscle mobility, and
  d) using the set of biomechanical components calculated in step (d) to calculate a biomechanical integrity score.

BRIEF DESCRIPTION OF DRAWINGS

The patent or application the contains at least one drawing executed in color. Copies of this patent or patent application publication with color drawing(s) will be provided by the Office upon request and payment of the necessary fee.

The subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through the use of the accompanying drawings, in which:

DETAILED DESCRIPTION OF THE INVENTION

Figure 1:
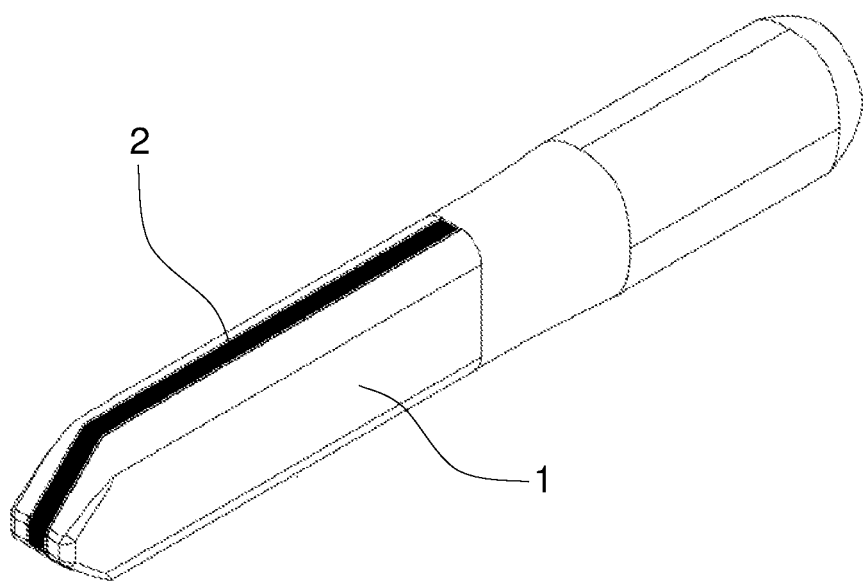
FIG. 1 is a perspective view of a vaginal tactile imaging probe.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Specific terms are used in the following description, which are defined as follows:

"Tactile sensor" is a sensor capable to measure an applied force averaged per sensor area or pressure thereon and transform it into an electrical signal to be used in tactile image formation.

"Stress" is a force per unit of area (pressure) measured at the surface of a vaginal wall (kPa).

"Tissue deformation" is used to describe vaginal wall and adjacent structures deformation generally in an orthogonal direction away from a vaginal canal—as caused by a movement of the tactile probe.

"Strain" is a soft tissue displacement under tissue deformation (mm).

"Tissue elasticity" is the capability of soft tissue (1) to resist against the applied load at relatively small deformation (between 0 and 15 mm) and (2) to return back after the applied load was removed; tissue elasticity is estimated as a ratio of stress to strain (kPa/mm).

"Pelvic floor support" is a capability of integrated pelvic structures in the posterior compartment to resist against the applied load at significant (above 15 mm and up to 45 mm) deformation, which is calculated as a ratio of stress to strain (kPa/mm).

"Muscle function" is the capability of muscle to produce an action including muscle contraction, relaxation, and mobility.

"Muscle strength" is the capability of muscle to generate force or pressure change on the vaginal wall during muscle contraction measured in kPa or N.

"Tactile Imaging" is a medical imaging modality that translates the sense of touch into a digital image. The tactile image is a function of P(x,y,z), where P is the pressure on soft tissue surface under applied deformation and x, y, and z are the coordinates where P was measured. The tactile image is a pressure map on which the direction of tissue deformation must be specified.

"Functional Tactile Imaging" translates muscle activity into dynamic pressure pattern P(x,y,t) for an area of interest, where t is time and x and y are coordinates where the pressure P was measured. It may include: (a) muscle voluntary contraction, (b) involuntary reflex contraction, (c) involuntary relaxation, and (d) specific maneuvers.

"Biomechanical Mapping" is used herein to describe a combination of "Tactile Imaging" plus "Functional Tactile Imaging".

"Vaginal Tactile Imager (VTI)" is a medical device to aid in the diagnosis and evaluation of vaginal and pelvic floor conditions. It allows assessment of tissue elasticity, pelvic floor support, and function. The target population comprises adults with pelvic organ prolapse, urinary incontinence, and tissue atrophy.

FIG. 1 presents a perspective view of vaginal tactile imaging (VTI) probe 1. The probe may have known dimensions. Probe 1 may contain a tactile array 2 configured to record tactile signals (pressure patterns), such as for example from two opposite sides along the entire length of the vagina. As the probe dimensions are known and fixed, tactile responses from the tactile array sensors may be translated into useful measurements of biomechanical parameters using known probe dimensions and recorded probe movements. Probe 1 may have an angled tip covered by the tactile sensors to record the pressure patterns on the vaginal walls during the probe insertion. The tactile imaging probe 1 may be equipped with a pressure sensor array mounted on its external surface that acts similar to human fingers during a clinical examination. Movements of the probe may be used for deforming the soft tissue under examination and detecting the resulting changes in the pressure pattern on the probe's surface. The sensor head may be moved over the surface of the tissue to be studied, and the pressure response is evaluated at multiple locations along the tissue. The results and tactile response data may be used to generate 2D/3D images showing pressure distribution over the area of the tissue under study.

Figure 2:
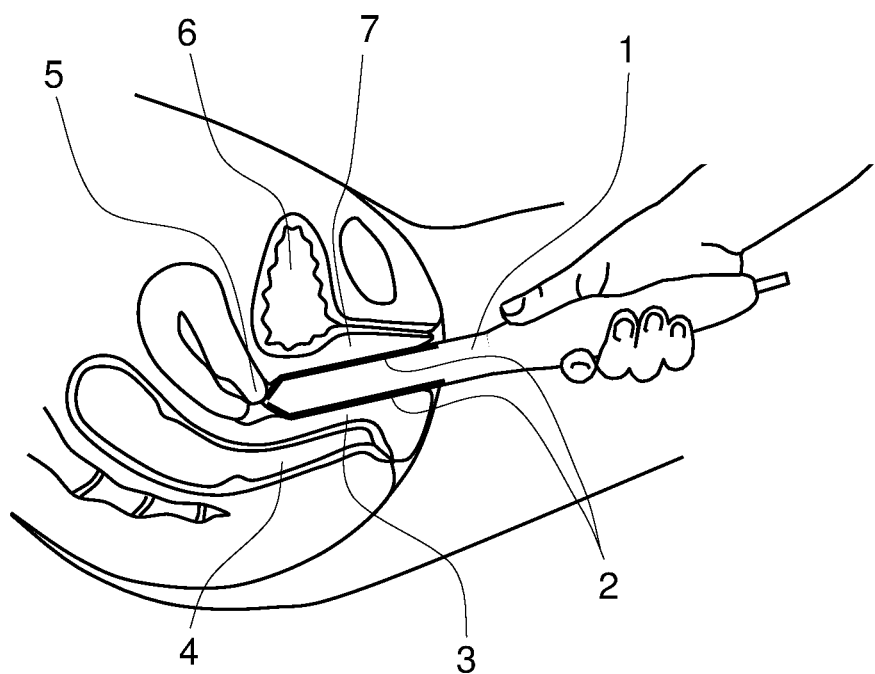
FIG. 2 is an illustration of a vaginal probe design and probe location after its insertion during recording of tactile response patterns from two opposing vaginal walls—anterior and posterior compartments.

FIG. 2 illustrates the vaginal tactile imaging probe 1 positioned in the vagina for the recording of pressure/tactile patterns by tactile sensor arrays 2 (thick black lines) from two opposing vaginal walls. The tactile patterns may be recorded for the anterior 7 and the opposing posterior 3 vaginal compartments as well as for the left and right sides of the vagina. Cervix 5 may be used as a reference point in presenting and analyzing tactile responses to vaginal tissue deformations and dynamic pressure patterns during pelvic muscle contraction. Rectum 4 and bladder 6 are shown as anatomical landmarks.

The vaginal tactile imaging probe 1, as shown in FIG. 2, may be equipped with a plurality of pressure (tactile) sensors spaced at 2.5 mm consecutively on both sides of the probe (96 individual sensors in one example), an orientation sensor, and a temperature controller configured to bring the probe temperature close to a human body before the examination. The tactile imaging data may be sampled from the probe sensors and displayed on the VTI monitor in real-time. The resulting pressure maps (tactile images) of the vagina integrate all the acquired pressure and positioning data for each of the pressure sensing elements. Additionally, the VTI may record the dynamic contraction of pelvic floor muscles with sufficient resolution, for example, a resolution of at least 1 mm. A lubricating jelly may be used for patient comfort and to provide reproducible boundary/contact conditions with deformed tissues.

A VTI probe 1 may be sized to cause anywhere between 3-15 mm of tissue displacement and deformation, for example resulting from the probe initial insertion (Test 1). The probe may be subsequently moved to cause anywhere between 15-45 mm of tissue deformation from the probe elevation (Test 2), and 5-7 mm of tissue deformation resulting from the probe rotation (Test 3). The probe may also be used for the recording of dynamic tactile responses during pelvic muscle contractions (Tests 4-8). The probe maneuvers in Tests 1-3 allow the accumulation of multiple pressure patterns from the tissue surface to compose an integrated tactile image for the investigated area using probe orientation data. The spatial gradients dP(x,y)/dy for anterior and posterior compartments may be calculated within the acquired tactile images in Tests 1 and 2; y-coordinate may be directed orthogonally from the longitudinal axis of the vaginal canal, x-coordinate may be located along the vaginal canal. The VTI probe may be equipped with a microprocessor containing software including data recording and analysis tools and reporting functions. It may be configured to present a visual representation of the anatomy, tactile pressure maps, and calculate (automatically) a plurality of predetermined parameters for at least some or all of the test procedures.

The pelvic examination procedure using a VTI probe may consist of eight tests which can be divided into three groups:

a. Low tissue deformation tests by moving a probe, when vaginal tissue is displaced from about 3 mm to about 15 mm in order to characterize tissue elasticity:
   Probe insertion,
   Probe rotation, b. Significant tissue deformation tests by moving a probe, when vaginal tissue is displaced from about 15 mm to about 45 mm in order to characterize pelvic floor support structures:
   Probe elevation, c. No tissue deformation tests (beyond initial probe insertion), when the probe is kept stationary and the patient is asked to perform actions causing voluntary and involuntary pelvic muscle contraction and relaxation in order to characterize dynamic pelvic function:
   Valsalva maneuver,
   Voluntary muscle contraction, (anterior versus posterior),
   Voluntary muscle contraction (left side versus right side),
   Involuntary relaxation, and
   Reflex muscle contraction (resulting from a patient's cough).

Tests 1, 2, 4, 5, 7 and 8 provide data for anterior/posterior compartments; Test 3 (probe rotation) for 360 degrees along the entire vagina, and Test 6 provides data for left/right sides (see Table 1).

TABLE 1

Exemplary VTI Examination includes 8 procedure tests.

| Test No. | Procedure | Output |
|---|---|---|
| Test 1 | Probe insertion | Tactile image for vaginal anterior and posterior compartments along the entire vagina (resistance, force, work, tissue elasticity) |
| Test 2 | Probe elevation | Tactile image for anterior and posterior compartments which related to pelvic floor support structures (pressure value sand pressure gradients for specified/critical locations) |
| Test 3 | Probe rotation | Tactile images for 360 degrees along the entire vagina (force and pressure values for specified positions/locations) |
| Test 4 | Valsalva maneuver | Dynamic pressure response from opposite sites (anterior versus posterior) along the entire vagina (changes in force and pressure; pressure peak displacements). |
| Test 5 | Voluntary muscle contraction | Dynamic pressure response from opposite sites (anterior versus posterior) along the entire vagina (changes in force and pressure; maximum pressure values). |
| Test 6 | Voluntary muscle contraction (sides) | Dynamic pressure response from opposite sides (left versus right) along the entire vagina (changes in force and pressure; maximum pressure values). |
| Test 7 | Involuntary relaxation | Dynamic pressure response from opposite sites (anterior versus posterior) along the entire vagina (changes in pressure). |
| Test 8 | Reflex muscle contraction (resulting from a cough) | Dynamic pressure response from opposite sites (anterior versus posterior) along the entire vagina (changes in force and pressure; pressure peak displacements). |

Figure 3:
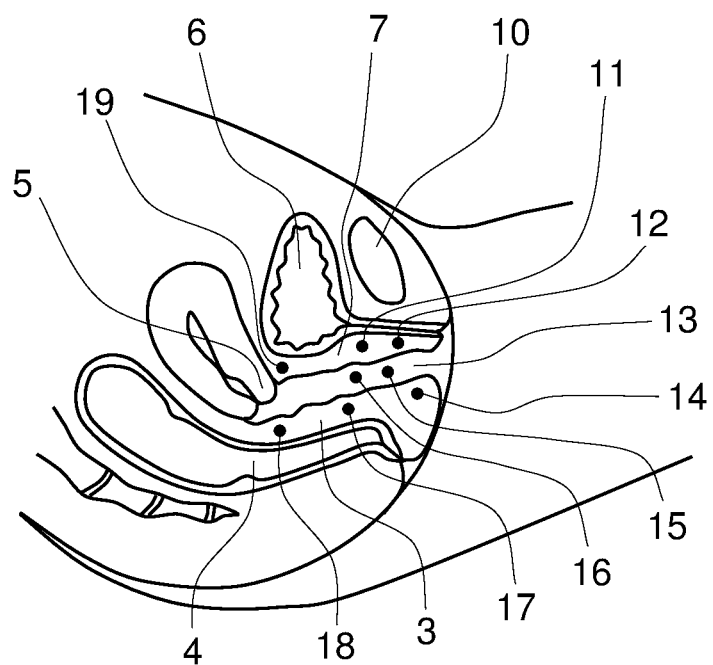
FIG. 3 is a schematic diagram to show anatomical locations for collecting tactile response data used for calculation of biomechanical parameters within the female pelvic floor.

FIG. 3 shows anatomical locations within the female pelvic floor where the tactile/pressure response parameters were measured by the VTI. Specifically, location 12 captures anterior aspects opposite to a pubic bone 10; location 11 provides responses from a urethra (not shown); location 19 characterizes apical anterior part connected to cervix 5; location 14 is related to Level III pelvic support; location 17 is related to Level II pelvic support; location 18 is related to Level I pelvic support; location 15 is related to vaginal side 1; and location 16 is related to vaginal side 2. Rectum 4 and bladder 6 are shown as anatomical landmarks.

Table 2 starting on the next page provides further details and an explanation of all 52 exemplary biomechanical parameters derived from the VII examination data.

TABLE 2

VTI Biomechanical Parameters

| Parameter No. | VTI Test | Parameters Abbreviation | Units | Parameter Description | Parameter Interpretation | Parameter Class | Targeting/ Contributing Pelvic Structures |
|---|---|---|---|---|---|---|---|
| 1 | 1 | Fmax | N | Maximum value of force measured during the VTI probe insertion | Maximum resistance of anterior vs posterior widening; tissue elasticity at specified location (capability to resist to applied deformation) | Maximum vaginal tissue elasticity at specified location | Tissues behind the anterior and posterior vaginal walls at 3-15 mm depth |
| 2 | 1 | Work | mJ | Work completed during probe insertion (Work = Force × Displacement) | Integral resistance of vaginal tissue (anterior and posterior) along the probe insertion | Average vaginal tissue elasticity | Tissues behind the anterior and posterior vaginal walls at 3-15 mm depth |
| 3 | 1 | Gmax_a | kPa/mm | Maximum value of anterior gradient (change of pressure per anterior wall displacement in orthogonal direction to the vaginal channel) | Maximum value of tissue elasticity in anterior compartment behind the vaginal at specified location | Maximum value of anterior tissue elasticity | Tissues/structures in anterior compartment at 10-15 mm depth |

TABLE 2-continued

VTI Biomechanical Parameters

| Parameter No. | VTI Test | Parameters Abbreviation | Units | Parameter Description | Parameter Interpretation | Parameter Class | Targeting/Contributing Pelvic Structures |
|---|---|---|---|---|---|---|---|
| 4 | 1 | Gmax_p | kPa/mm | Maximum value of posterior gradient (change of pressure per posterior wall displacement in orthogonal direction to the vaginal channel) | Maximum value of tissue elasticity in posterior compartment behind the vaginal at specified location | Maximum value of posterior tissue elasticity | Tissues/structures in anterior compartment at 10-15 mm depth |
| 5 | 1 | Pmax_a | kPa | Maximum value of pressure per anterior wall along the vagina | Maximum resistance of anterior tissue to vaginal wall deformation | Anterior tissue elasticity | Tissues/structures in anterior compartment |
| 6 | 1 | Pmax_p | kPa | Maximum value of pressure per posterior wall along the vagina | Maximum resistance of posterior tissue to vaginal wall deformation | Posterior tissue elasticity | Tissues/structures in posterior compartment |
| 7 | 2 | P1max_a | kPa | Maximum pressure at the area of pubic bone (anterior, 12 in FIG. 3) | Proximity of pubic bone to vaginal wall and perineal body strength | Anatomic aspects and tissue elasticity | Tissues between vagina and pubic bone; perineal body |
| 8 | 2 | P2max_a | kPa | Maximum pressure at the area of urethra (anterior, 11 in FIG. 3) | Elasticity/mobility of urethra | Anatomic aspects and tissue elasticity | Urethra and surrounding tissues |
| 9 | 2 | P3max_a | kPa | Maximum pressure at the cervix area (anterior, 19 FIG. 3) | Mobility of uterus and conditions of uterosacral and cardinal ligaments | Pelvic floor support | Uterosacral and cardinal ligaments |
| 10 | 2 | P1max_p | kPa | Maximum pressure at the perineal body (posterior, see 14 in FIG. 3) | Pressure feedback of Level III support | Pelvic floor support | Puboperineal, puborectal muscles |
| 11 | 2 | P2max_p | kPa | Maximum pressure at middle third of vagina (posterior, see 17 in FIG. 3) | Pressure feedback of Level II support | Pelvic floor support | Pubovaginal, puboanal muscles |
| 12 | 2 | P3max_p | kPa | Maximum pressure at upper third of vagina (posterior, see 18 in FIG. 3) | Pressure feedback of Level I support | Pelvic floor support | Iliococcygeal muscle, levator plate |
| 13 | 2 | G1max_a | kPa/mm | Maximum gradient at the area of pubic bone (anterior, see 12 in Figure 3) | Vaginal elasticity at pubic bone area | Anterior tissue elasticity | Tissues between vagina and pubic bone; perineal body |
| 14 | 2 | G2max_a | kPa/mm | Maximum gradient at the area of urethra (anterior, see 11 in FIG. 3) | Mobility and elasticity of urethra | Urethral tissue elasticity | Urethra and surrounding tissues |
| 15 | 2 | G3max_a | kPa/mm | Maximum gradient at the cervix area (anterior, see 19 in FIG. 3) | Conditions of uterosacral and cardinal ligaments | Pelvic floor support | Uterosacral and cardinal ligaments |
| 16 | 2 | G1max_p | kPa/mm | Maximum gradient at the perineal body (posterior, see 14 in FIG. 3) | Strength of Level III support (tissue deformation up to 25 mm) | Pelvic floor support | Puboperineal, puborectal muscles |
| 17 | 2 | G2max_p | kPa/mm | Maximum gradient at middle third of vagina (posterior, see 17 in FIG. 3) | Strength of Level II support (tissue deformation up to 35 mm) | Pelvic floor support | Pubovaginal, puboanal muscles |
| 18 | 2 | G3max_p | kPa/mm | Maximum gradient at upper third of vagina (posterior, see 18 in FIG. 3) | Strength of Level I support (tissue deformation up to 45 mm) | Pelvic floor support | Iliococcygeal muscle, levator plate |
| 19 | 3 | Pmax | kPa | Maximum pressure at vaginal walls deformation by 7 mm | Hard tissue or tight vagina | Vaginal tissue elasticity | Tissues behind the vaginal walls at 5-7 mm depth |
| 20 | 3 | Fap | N | Force applied by anterior and posterior compartments to the probe | Integral strength of anterior and posterior compartments | Vaginal tightening | Tissues behind anterior/posterior vaginal walls. |
| 21 | 3 | Fs | N | Force applied by entire left and right sides of vagina to the probe | Integral strength of left and right sides of vagina | Vaginal tightening | Vaginal right/left walls and tissues behind them. |
| 22 | 3 | Pmax_s1 | kPa | Pressure response from a selected location (maximum 1) at left side (see 15 in FIG. 3) | Hard tissue on left vaginal wall | Irregularity on vaginal wall | Tissue/muscle behind the vaginal walls on left side. |
| 23 | 3 | Pmax_s2 | kPa | Pressure response from a selected location (maximum 2) at left side (see 16 in FIG. 3) | Hard tissue on left vaginal wall | Irregularity on vaginal wall | Tissue/muscle behind the vaginal walls on left side. |

TABLE 2-continued

VTI Biomechanical Parameters

| Parameter No. | VTI Test | Parameters Abbreviation | Units | Parameter Description | Parameter Interpretation | Parameter Class | Targeting/ Contributing Pelvic Structures |
|---|---|---|---|---|---|---|---|
| 24 | 3 | Pmax_s3 | kPa | Pressure response from a selected location (maximum 1) at right side (see 15 in FIG. 3) | Hard tissue on right vaginal wall | Irregularity on vaginal wall | Tissue/muscle behind the vaginal walls on right side. |
| 25 | 4 | dF_a | N | Integral force change in anterior compartment at Valsalva maneuver | Pelvic function at Valsalva maneuver | Pelvic function | Multiple pelvic muscles |
| 26 | 4 | dPmax_a | kPa | Maximum pressure change in anterior compartment at Valsalva maneuver. | Pelvic function at Valsalva maneuver | Pelvic function | Multiple pelvic muscles |
| 27 | 4 | dL_a | mm | Displacement of the maximum pressure peak in anterior compartment | Mobility of anterior structures, Valsalva maneuver | Pelvic function | Urethra, pubovaginal muscle; ligaments |
| 28 | 4 | dF_p | N | Integral force change in posterior compartment at Valsalva maneuver | Pelvic function at Valsalva maneuver | Pelvic function | Multiple pelvic muscles |
| 29 | 4 | dPmax_p | kPa | Maximum pressure change in posterior compartment at Valsalva maneuver. | Pelvic function at Valsalva maneuver | Pelvic function | Multiple pelvic muscles |
| 30 | 4 | dL_p | mm | Displacement of the maximum pressure peak in posterior compartment | Mobility of posterior structures Valsalva maneuver | Pelvic function | Anorectal, puborectal, pubovaginal muscles; ligaments |
| 31 | 5 | dF_a | N | Integral force change in anterior compartment at voluntary muscle contraction | Integral contraction strength of pelvic muscles along the vagina | Pelvic function | Puboperineal, puborectal, pubovaginal and iliococcygeal muscles; urethra |
| 32 | 5 | dPmax_a | kPa | Maximum pressure change in anterior compartment at voluntary muscle contraction | Contraction strength of specified pelvic muscles | Pelvic function | Puboperineal, puborectal and pubovaginal muscles |
| 33 | 5 | Pmax_a | kPa | Maximum pressure value in anterior compartment at voluntary muscle contraction. | Static and dynamic peak support of the pelvic floor | Pelvic function | Puboperineal and puborectal muscles |
| 34 | 5 | dF_p | N | Integral force change in posterior compartment at voluntary muscle contraction | Integral contraction strength of pelvic muscles along the vagina | Pelvic function | Puboperineal, puborectal, pubovaginal and iliococcygeal muscles |
| 35 | 5 | dPmax_p | kPa | Maximum pressure change in posterior compartment at voluntary muscle contraction | Contraction strength of pelvic muscles at specified location | Pelvic function | Puboperineal, puborectal and pubovaginal muscles |
| 36 | 5 | Pmax_p | kPa | Maximum pressure value in posterior compartment at voluntary muscle contraction. | Static and dynamic peak support of the pelvic floor | Pelvic function | Puboperineal and puborectal muscles |
| 37 | 6 | dF_r | N | Integral force change in right side at voluntary muscle contraction | Integral contraction strength of pelvic muscles along the vagina | Pelvic function | Puboperineal, puborectal, and pubovaginal muscles |
| 38 | 6 | dPmax_r | kPa | Maximum pressure change in right side at voluntary muscle contraction | Contraction strength of specific pelvic muscle | Pelvic function | Puboperineal or puborectal or pubovaginal muscles |
| 39 | 6 | Pmaxa_r | kPa | Maximum pressure value in right side at voluntary muscle contraction | Specified pelvic muscle contractive capability and integrity | Pelvic function | Puboperineal or puborectal muscles |
| 40 | 6 | dF_l | N | Integral force change in left side at voluntary muscle contraction | Integral contraction strength of pelvic muscles along the vagina | Pelvic function | Puboperineal, puborectal, and pubovaginal muscles |
| 41 | 6 | dPmax_l | kPa | Maximum pressure change in left side at voluntary muscle contraction | Contraction strength of specific pelvic muscle | Pelvic function | Puboperineal or puborectal or pubovaginal muscles |

TABLE 2-continued

VTI Biomechanical Parameters

| Parameter No. | VTI Test | Parameters Abbreviation | Units | Parameter Description | Parameter Interpretation | Parameter Class | Targeting/ Contributing Pelvic Structures |
|---|---|---|---|---|---|---|---|
| 42 | 6 | Pmaxa_l | kPa | Maximum pressure value in left side at voluntary muscle contraction | Specified pelvic muscle contractive capability and integrity | Pelvic function | Puboperineal or puborectal muscles |
| 43 | 7 | dPdt_a | kPa/s | Anterior absolute pressure change per second for maximum pressure at involuntary relaxation | Innervation status of specified pelvic muscles | Innervations status | Levator ani muscles |
| 44 | 7 | dpcdt_a | %/s | Anterior relative pressure change per second for maximum pressure at involuntary relaxation | Innervation status of specified pelvic muscles | Innervations status | Levator ani muscles |
| 45 | 7 | dPdt_p | kPa/s | Posterior absolute pressure change per second for maximum pressure at involuntary relaxation | Innervation status of specified pelvic muscles | Innervations status | Levator ani muscles |
| 46 | 7 | dpcdt_p | %/s | Posterior relative pressure change per second for maximum pressure at involuntary relaxation | Innervation status of specified pelvic muscles | Innervations status | Levator ani muscles |
| 47 | 8 | dF_a | N | Integral force change in anterior compartment at reflex pelvic muscle contraction (cough) | Integral pelvic function at reflex muscle contraction | Pelvic function | Multiple pelvic muscle |
| 48 | 8 | dPmax_a | kPa | Maximum pressure change in anterior compartment at reflex pelvic muscle contraction (cough). | Contraction strength of specified pelvic muscles | Pelvic function | Multiple pelvic muscle |
| 49 | 8 | dL_a | mm | Displacement of the maximum pressure peak in anterior compartment | Mobility of anterior structures at reflex muscle contraction | Pelvic function | Urethra, pubovaginal muscle; ligaments |
| 50 | 8 | dF_p | N | Integral force change in posterior compartment at reflex pelvic muscle contraction (cough) | Integral pelvic function at reflex muscle contraction | Pelvic function | Multiple pelvic muscle |
| 51 | 8 | dPmax_p | kPa | Maximum pressure change in posterior compartment at reflex pelvic muscle contraction (cough). | Contraction strength of specified pelvic muscles | Pelvic function | Multiple pelvic muscle |
| 52 | 8 | dL_p | mm | Displacement of the maximum pressure peak in posterior compartment | Mobility of anterior structures at reflex muscle contraction | Pelvic function | Anorectal, puborectal and pubovaginal muscles; ligaments |

Example 1: Data from a Clinical Study

The analyzed dataset in this study includes 253 subjects; 125 subjects had normal pelvic floor conditions and 128 subjects had POP stage II+. These subjects were examined with the VII probe in the scope multi-site observational, case-controlled studies completed in 2014-2018 (clinical trials identifiers NCT02294383 and NCT02925585) and ongoing study with VTI11 protocol. It was important that all the analyzed subjects did not have any prior pelvic surgery. Table 3 presents the mean and standard deviation for the subject's age, parity, weight, and height separately for normal and POP groups. The VTI examination data for the eight Tests (see Table 1) were obtained and recorded at the time of the scheduled urogynecological visits.

The total study workflow comprised the following steps: (1) Recruiting women who did not previously have a pelvic surgery and had normal pelvic floor conditions (no POP) or had POP stage II or higher; (2) Acquiring clinical diagnostic information related to the cases included in the study by standard clinical means; (3) Performing a VTI examination in lithotomic position; and (4) Analyzing VTI data. Before the VTI examination, a standard physical examination was performed, including a bimanual pelvic examination and Pelvic Organ Prolapse Quantification (POP-Q). The pelvic floor conditions were categorized by the stage of the prolapse based on the maximum stage from anterior, posterior, and uterine prolapse. Employing this approach, we found that 68 subjects had POP stage II, 57 had stage III, and three had stage IV.

Statistical Methods

A total of 52 biomechanical parameters were calculated automatically by the VTI software per each of the 253 analyzed VTI examination data. The two-sample t-test ($p<0.05$) was employed to test the null hypothesis that the data in normal and POP groups have equal means and equal variances. The alternative hypothesis is that the data in these groups come from populations with unequal means. P-values for testing the hypothesis were calculated. Pearson's linear correlation coefficients (r) were calculated among 52 VTI parameters, each parameter against all other 51 parameters. For the visual evaluation of the analyzed data distributions, notched boxplots showing a confidence interval for the median value (central vertical line), 25% and 75% quartiles were used. The spacing between the different parts of the box helps to compare variance. The boxplot also determines skewness (asymmetry) and outlier (cross).

Composition of Biomechanical Integrity Score

Figure 4A:
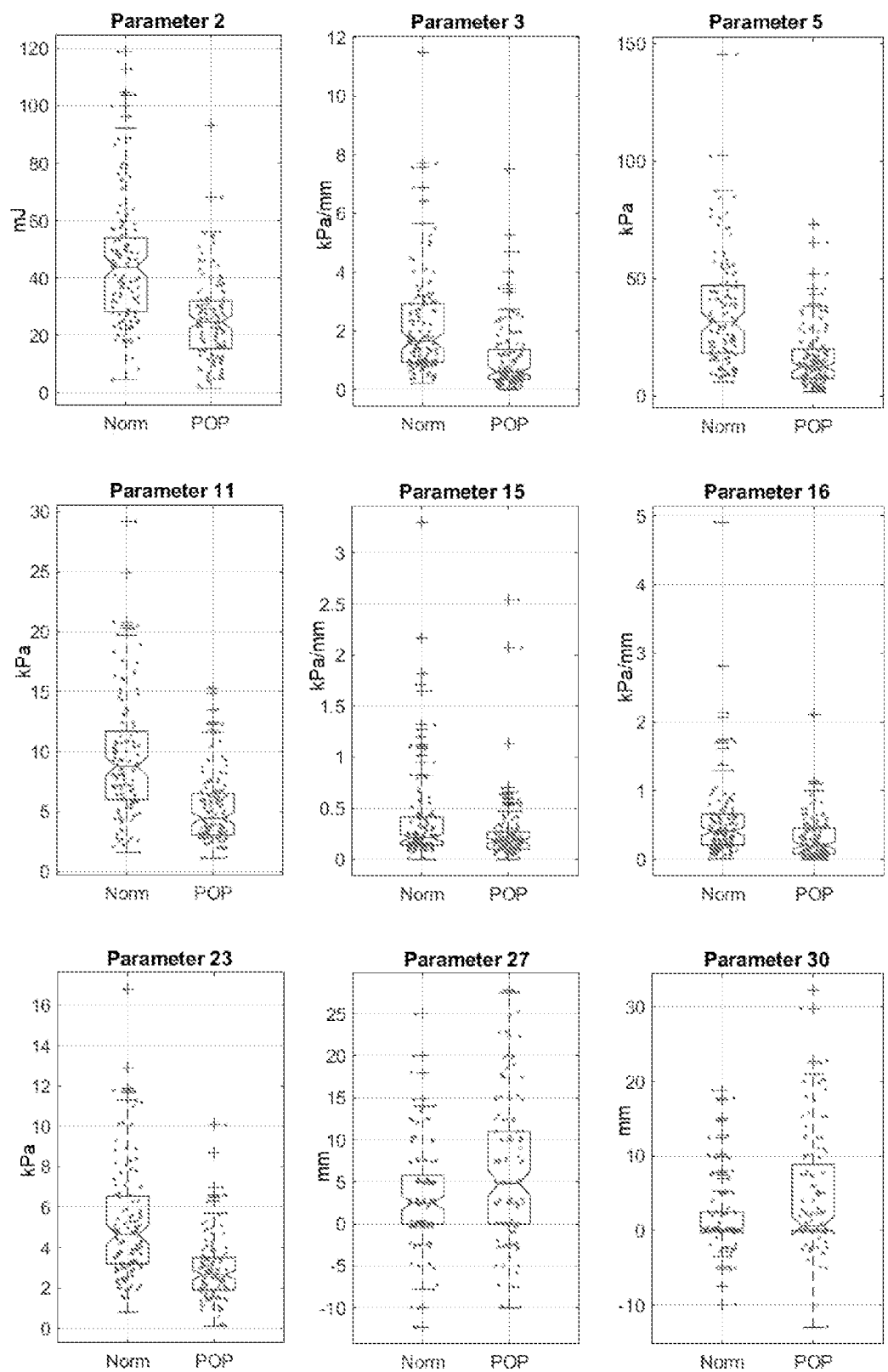
FIGS. 4a, 4b, 4c show various boxplots for selected 26 VTI parameters, identified as demonstrating statistically significant sensitivity to POP conditions and not highly correlated with each other.
Figure 4B:
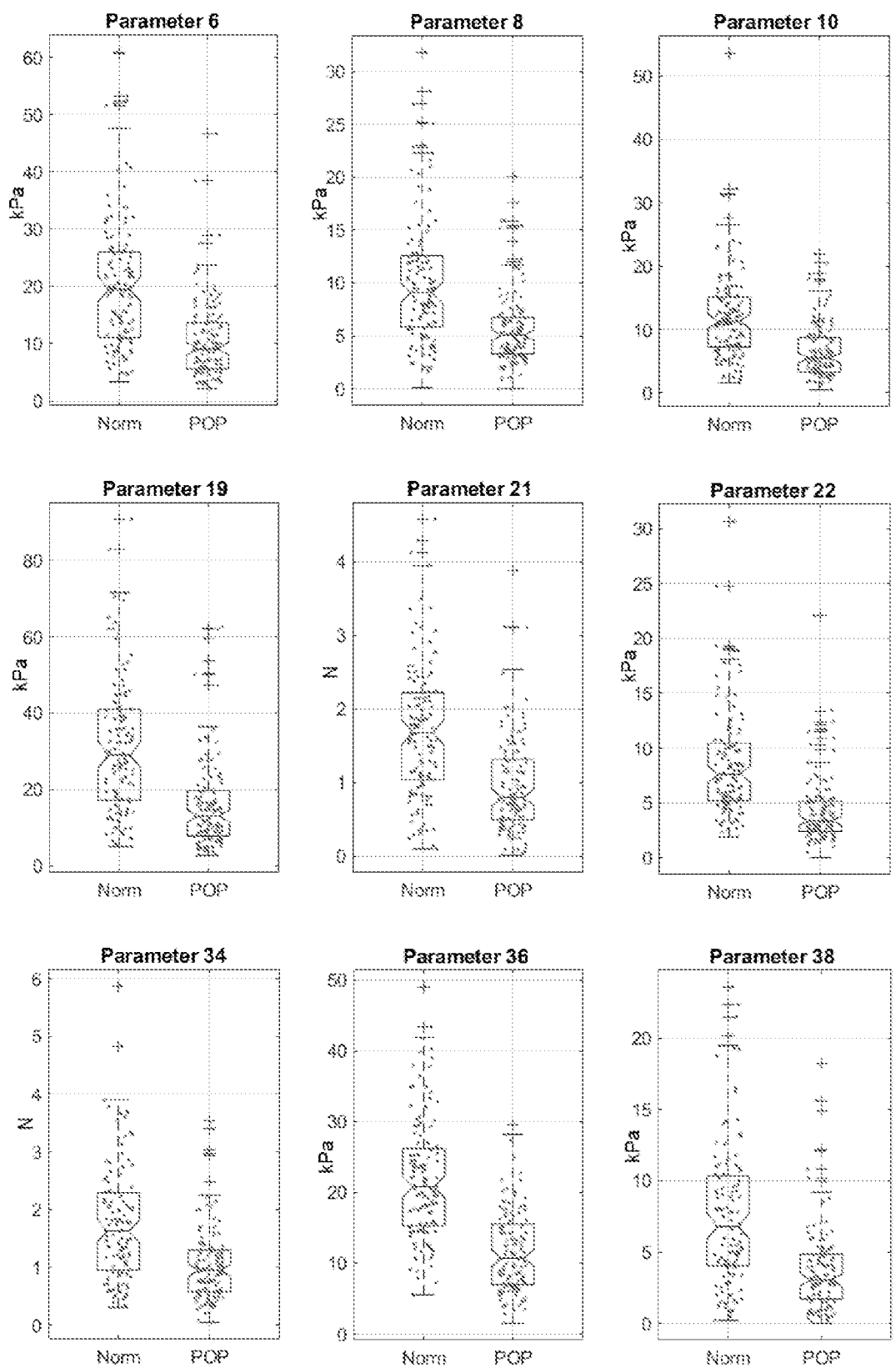
Figure 4C:
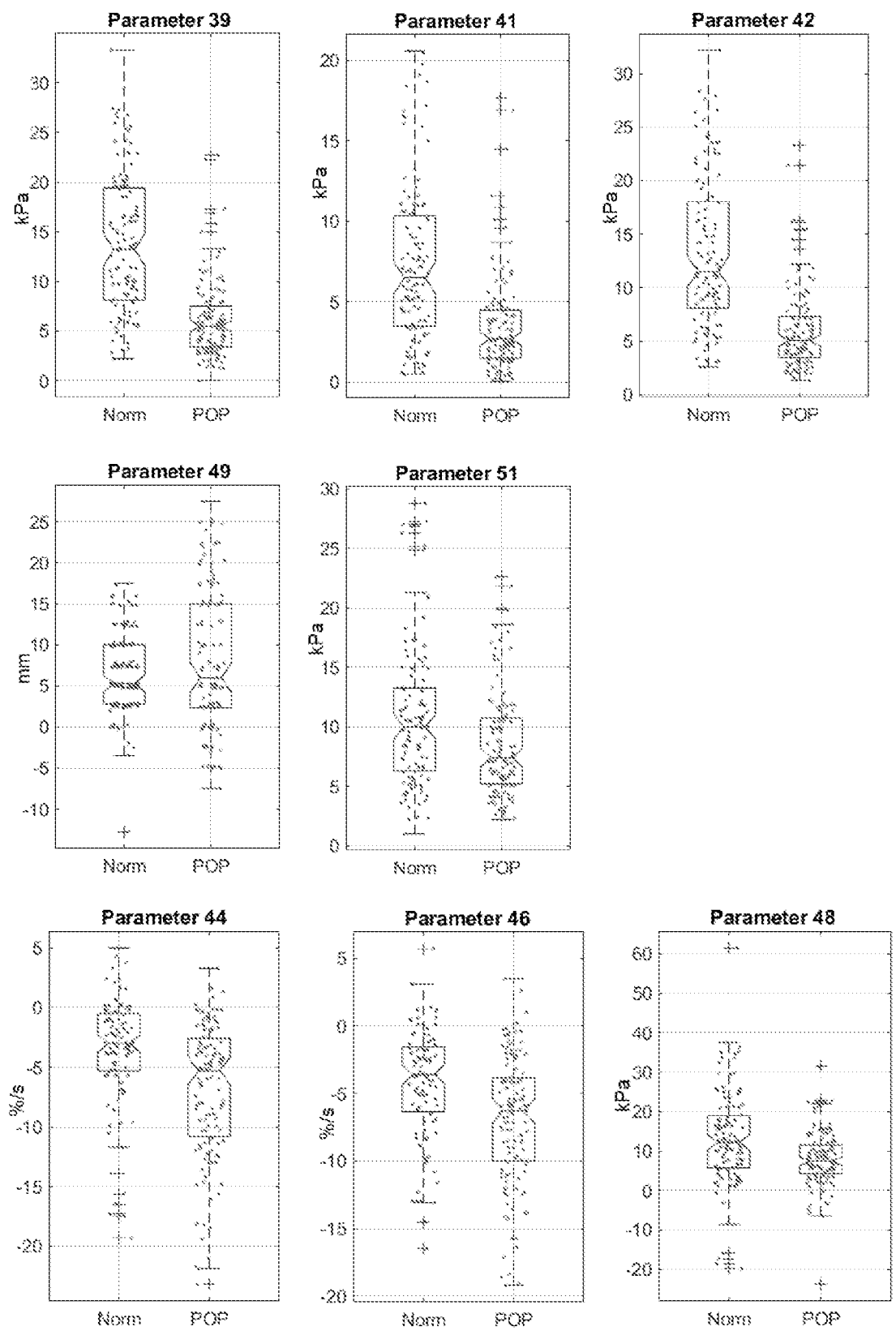

Selecting VTI parameters with significant changes at POP versus the normal pelvic conditions was deemed necessary. Two specific quantitative criteria were imposed on such selection: (1) a t-test p<0.05 for the sub-set data of 128 POP cases against the sub-set data for 125 normal cases and (2) a correlation coefficient r<0.85 with all other parameters. 40 parameters passed the first criteria, and only 26 parameters passed both the first and the second criteria. FIGS. 4a, 4b, 4c present the boxplots, and Table 3 shows the numerical data for these selected 26 VTI parameters responsive to POP and not highly correlated with each other. For consistency, the numbering of the VTI parameters in the figures is kept exactly as in Table 2.

relaxation parameters, which have a negative sign because muscle force involuntary goes down, are increasing by 65.3% and 90.0% in POP—relaxation develops faster. The muscle mobility parameters, which may have a negative or a positive sign, are increasing by 79.0% and 167.0% in POP—as muscle mobility develops along the vagina. The mean subject's age and parity in the normal and POP groups are significantly different: 36 versus 65.5 years old and 0.9 versus 2.4 respectively. That is the intended difference in the analyzed groups because, for the reference (zero-line in the Biomechanical Integrity Score), a younger population is needed without POP, which develops with age. The mean subject's weight and height are the same in both groups (see the last part of Table 3).

The last column in Table 3 brings p-values for the two-sample t-tests (normal versus POP). The p-values for the VTI parameters are found in the range of $1.2 \times 10^{-23}$ to $4.8 \times 10^{-2}$; most of the p-values being below $1.0 \times 10^{-5}$. The p-value for the biomechanical integrity score has $p=4.3 \times 10^{-31}$ for two analyzed groups. It indicates that the data in these groups come from populations with unequal means and strong sensitivity to POP conditions.

The parameters listed in Table 3 have different units (see column 5 in Table 3). The next step in data analysis is to bring all the selected parameters to uniform units to allow

TABLE 3

VTI parameters and Biomechanical Integrity Score sensitivity to POP conditions, and demographic data for the studied groups.

| Parameter* | Test No. | Biomechanical Integrity Score Component | Parameter Weight | Units | Norm Mean (n = 125) | Norm STD (n = 125) | POP Mean (n = 128) | POP STD (n = 128) | 100%*(POP-Norm)/Norm | Norm vs POP p-value |
|---|---|---|---|---|---|---|---|---|---|---|
| 2 | 1 | Elasticity | 0.125 | mJ | 45.4 | 22.4 | 25.4 | 14.7 | −44.1% | 4.1E−15 |
| 3 | 1 | Elasticity | 0.125 | kPa/mm | 2.18 | 1.76 | 1.05 | 1.14 | −51.9% | 5.8E−09 |
| 5 | 1 | Elasticity | 0.125 | kPa | 35.7 | 23.1 | 16.0 | 12.6 | −55.1% | 3.6E−15 |
| 6 | 1 | Elasticity | 0.125 | kPa | 20.6 | 12.0 | 10.8 | 7.08 | −47.5% | 1.2E−13 |
| 8 | 2 | Support | 0.200 | kPa | 10.1 | 6.09 | 5.77 | 3.79 | −43.3% | 6.8E−11 |
| 10 | 2 | Support | 0.200 | kPa | 12.2 | 7.33 | 6.61 | 4.25 | −46.0% | 1.1E−12 |
| 11 | 2 | Support | 0.200 | kPa | 9.52 | 5.07 | 5.22 | 2.87 | −45.2% | 5.3E−15 |
| 15 | 2 | Support | 0.200 | kPa/mm | 0.38 | 0.47 | 0.25 | 0.31 | −35.6% | 6.8E−03 |
| 16 | 2 | Support | 0.200 | kPa/mm | 0.55 | 0.60 | 0.30 | 0.30 | −45.9% | 3.6E−05 |
| 19 | 3 | Elasticity | 0.125 | kPa | 31.4 | 17.7 | 16.1 | 12.3 | −48.7% | 5.7E−14 |
| 21 | 3 | Elasticity | 0.125 | N | 1.71 | 0.90 | 0.96 | 0.67 | −43.6% | 1.3E−12 |
| 22 | 3 | Elasticity | 0.125 | kPa | 8.66 | 4.90 | 4.26 | 3.01 | −50.8% | 8.3E−16 |
| 23 | 3 | Elasticity | 0.125 | kPa | 5.16 | 2.82 | 2.95 | 1.64 | −42.9% | 4.1E−13 |
| 27 | 4 | Mobility | 0.400 | mm | 3.26 | 6.17 | 5.83 | 8.54 | 79.0% | 7.9E−03 |
| 30 | 4 | Mobility | 0.400 | mm | 1.71 | 4.97 | 4.56 | 7.86 | 167.0% | 8.9E−04 |
| 34 | 5 | Contraction | 0.200 | N | 1.77 | 1.01 | 1.05 | 0.66 | −40.3% | 1.9E−10 |
| 36 | 5 | Contraction | 0.200 | kPa | 21.8 | 8.55 | 11.6 | 5.76 | −46.7% | 1.2E−23 |
| 38 | 6 | Contraction | 0.100 | kPa | 7.55 | 5.12 | 3.79 | 3.17 | −49.8% | 2.3E−11 |
| 39 | 6 | Contraction | 0.100 | kPa | 13.7 | 7.06 | 6.10 | 3.92 | −55.7% | 4.9E−22 |
| 41 | 6 | Contraction | 0.100 | kPa | 7.29 | 4.92 | 3.58 | 3.11 | −50.9% | 9.7E−12 |
| 42 | 6 | Contraction | 0.100 | kPa | 13.2 | 6.97 | 6.06 | 3.93 | −54.4% | 2.0E−20 |
| 44 | 7 | Relaxation | 0.500 | %/s | −3.68 | 4.75 | −6.99 | 5.70 | 90.0% | 3.0E−06 |
| 46 | 7 | Relaxation | 0.500 | %/s | −4.20 | 4.10 | −6.95 | 4.79 | 65.3% | 5.0E−06 |
| 48 | 8 | Contraction | 0.100 | kPa | 12.9 | 12.2 | 7.84 | 6.86 | −39.4% | 8.5E−05 |
| 49 | 8 | Mobility | 0.200 | mm | 6.55 | 4.95 | 8.01 | 8.55 | 22.4% | 4.8E−02 |
| 51 | 8 | Contraction | 0.100 | kPa | 10.8 | 6.00 | 8.59 | 4.58 | −20.5% | 1.4E−03 |
| Biomechanical Integrity Score | | | | SD | −0.05 | 1.00 | −1.60 | 0.84 | — | 4.3E−31 |
| Patient Age | | | | year | 36.0 | 15.0 | 65.5 | 11.5 | 81.9% | 2.6E−35 |
| Patient Parity | | | | — | 0.9 | 1.0 | 2.4 | 1.1 | 166.7% | 2.5E−25 |
| Patient Weight | | | | kg | 69.5 | 14.3 | 70.0 | 12.9 | 0.7% | 7.6E−01 |
| Patient Height | | | | cm | 163.2 | 9.6 | 162.3 | 7.7 | −0.6% | 4.4E−01 |

*parameter numbering is same as in Table 2

The tenth column in Table 3 may be used to assess the extent of each VTI parameter change in POP population relative to population with the normal pelvic conditions. The elasticity parameters are decreasing by −42.9% . . . −55.1% in POP, the pelvic support parameters are decreasing by −35.6% . . . −46.0%, and the muscle contraction parameters are decreasing by −40.3% . . . −55.7% in POP. The muscle their arithmetic combination. For this analysis, the preference to the units of standard deviation was provided although other approaches may also be used as can be recognized by those skilled in the art. All VTI data were transformed according to equation 1 below.

$$Psd_{ni} = (Po_{ni} - Pa_n)/SD_n \quad (1)$$

Here, $Po_{ni}$ is an original value of the n-parameter for i-subject; $Pa_n$ is an arithmetic average of the n-parameter for subjects aged 18-39 years in the group with normal pelvic conditions (92 out of 125 subjects); $SD_n$ is a standard deviation for the n-parameter for 125 subjects in the group with normal pelvic conditions; and $Psd_{ni}$ is the transformed value of the n-parameter for i-subject in units of standard deviation.

Selected Biomechanical Parameters

A subset of the original 52 biomechanical parameters was selected as representing parameters that are indicative of the POP vs. normal condition. The rest of the 52 biomechanical parameters were discarded for the purposes of calculating the biomechanical integrity score. The following is a more detailed description of the 26 selected biomechanical parameters and methods of calculating thereof in the same order as listed in the previous tables.

Test 1: Parameter 2—Average Vaginal Tissue Elasticity

The average tissue elasticity is calculated as Work completed by an operator during the probe insertion into a vagina. The vaginal probe has a double-sided angled tip which moves the anterior and posterior walls in orthogonal directions from the vaginal canal (probe insertion line). The force applied to the probe $F(x)$ along the vaginal canal (vaginal resistance, x is a coordinate along the vaginal canal) is calculated of pressure distribution $P_{tip}$ on the probe tip under angle $\alpha$ of the probe and its contact area $A_{tip}$ with vaginal tissue according to the expression (2). The amount of Work done is given by the probe force $F(x)$ multiplied by the probe displacement $\Delta x$ during the probe insertion into the vagina up to the cervix according to the expression (3). This parameter has units of Joule [J=N×m] or millijoule [mJ].

$$F(x)=\cos(\alpha)\times\Sigma_{probe\ tip}(P_{tip}\times A_{tip}) \quad (2)$$

$$\text{Work}=\Sigma_{x=0\ \ldots\ cervix}(F(x)\times\Delta x) \quad (3)$$

Test 1: Parameter 3—Maximum Anterior Pressure Gradient

Maximum anterior pressure gradient (change of pressure per anterior wall displacement, $\Delta P_{tip}(x)/\Delta y$, in orthogonal y-direction to the vaginal canal) is calculated for every probe x-position during the probe insertion along the vaginal canal. We defined this parameter Gmax_a as the maximum stress/strain ratio according to the expression (4) below in units of [kPa/mm]. This parameter characterizes the maximum anterior tissue elasticity along the vagina.

$$G\text{max}\_a=\max_{x=0\ \ldots\ cervix}\{\Delta P_{tip}(x)/\Delta y\} \quad (4)$$

Test 1: Parameter 5—Maximum Anterior Pressure

During the probe insertion into a vagina, maximum anterior pressure Pmax_a is defined according to the expression (5). This parameter has units of [kPa] and characterizes stress at known tissue displacement (strain) at probe insertion.

$$P\text{max}\_a=\max_{x=0\ \ldots\ cervix}\{P_{tip\_anterior}(x)\} \quad (5)$$

Test 1: Parameter 6—Maximum Posterior Pressure

During the probe insertion into a vagina, maximum posterior pressure Pmax_p is defined according to the expression (6). This parameter has units of [kPa] and characterizes stress at known tissue displacement (strain) at probe insertion.

$$P\text{max}\_p=\max_{x=0\ \ldots\ cervix}\{P_{tip\_posterior}(x)\} \quad (6)$$

Test 2: Parameter 8—Maximum Pressure at Urethral Area

During the elevation in a vagina, maximum anterior pressure P2max_a at location 11 (urethral area) in FIG. 3 is defined according to the expression (6). This parameter has units of [kPa] and characterizes stress at known tissue displacement (strain) at probe elevation. Applied relatively high tissue deformation (>10 mm) for this area characterizes the pelvic support capability.

$$P2\text{max}\_a=\max_{x=urethral\_area}\{P_{anterior}(x)\} \quad (7)$$

Test 2: Parameter 10—Maximum Pressure at Perineal Area

During the probe elevation in a vagina, maximum posterior pressure P1max_p at location 14 (perineal area) in FIG. 3 is defined according to the expression (8). This parameter has units of [kPa] and characterizes stress at known tissue displacement (strain) at probe elevation. Applied relatively high tissue deformation (>10 mm) for this area characterizes the pelvic support capability.

$$P1\text{max}\_p=\max_{x=perineal\_area}\{P_{posterior}(x)\} \quad (8)$$

Test 2: Parameter 11—Maximum Mid Posterior Pressure

During the probe elevation in a vagina, maximum posterior pressure P2max_p at location 17 (mid posterior area) in FIG. 3 is defined according to the expression (9). This parameter has units of [kPa] and characterizes stress at known tissue displacement (strain) at probe elevation. Applied relatively high tissue deformation (>15 mm) for this area characterizes the pelvic support capability.

$$P2\text{max}\_p=\max_{x=mid\_area}\{P_{posterior}(x)\} \quad (9)$$

Test 2: Parameter 15—Maximum Cervical Pressure Gradient

Maximum cervical pressure gradient (change of pressure per anterior wall displacement, $\Delta P_{anterior}(x)/\Delta y$, in orthogonal y-direction to the vaginal canal) is calculated for cervical area 19 in FIG. 3 during the probe elevation. We defined this parameter G3max_a as the maximum stress/strain ratio according to the expression (10) below in units of [kPa/mm]. This parameter characterizes the pelvic support.

$$G3\text{max}\_a=\max_{x=cervical\_area}\{\Delta P_{anterior}(x)/\Delta y\} \quad (10)$$

Test 2: Parameter 16—Maximum Perineal Pressure Gradient

Maximum perineal pressure gradient (change of pressure per anterior wall displacement, $\Delta P_{anterior}(X)/\Delta y$, in orthogonal y-direction to the vaginal canal) is calculated for perineal area 14 in FIG. 3 during the probe elevation. We defined this parameter G1max_p as maximum stress/strain ratio according to the expression (11) below in units of [kPa/mm]. This parameter characterizes the pelvic support.

$$G1\text{max}\_p=\max_{x=perineal\_area}\{\Delta P_{posterior}(x)/\Delta y\} \quad (11)$$

Test 3: Parameter 19—Maximum Pressure at Vaginal Walls

During the probe rotation through an angle $\Omega=0\ldots 360$ degrees inside the vagina, we can define the maximum pressure Pmax in the vagina according to the expression (12). This parameter has units of [kPa] and characterizes stress at known tissue displacement (strain) at probe rotation.

$$P\text{max}=\max_{x=0\ \ldots\ cervix}\{P(x,\Omega)\} \quad (12)$$

Test 3: Parameter 21—Vaginal Side Tightening

This Fs force according to expression (15) is calculated as a cumulative force applied to all 96 pressure sensors when the tactile sensitive area comes in contact with the left side of the vagina producing F_left force (see expression 13) and with by the right side of vagina producing F_right (see expression 14). This parameter has units of [N] and characterizes stress at known tissue displacement (strain) at probe rotation.

$$F\_left = \Sigma_{x=0 \ldots cervix}(P_{left}(x) \times A_{left}(x)) \qquad (13)$$

$$F\_right = \Sigma_{x=0 \ldots cervix}(P_{right}(x) \times A_{right}(x)) \qquad (14)$$

$$Fs = \Sigma_{x=0 \ldots cervix}(F\_left + F\_right) \qquad (15)$$

Test 3: Parameter 22—Maximum Left Side Pressure 1

During the probe rotation in vagina, maximum left side pressure Pmax_s1 at location 15 in FIG. 3 is defined according to the expression (16). This location corresponds the perineal part of vagina. This parameter has units of [kPa] and characterizes stress at known tissue displacement (strain) at probe rotation.

$$Pmax\_s1 = \max_{x=perineal}\{P_{left\_side}(x)\} \qquad (16)$$

Test 3: Parameter 23—Maximum Left Side Pressure 2

During the probe rotation in vagina, maximum left-side pressure Pmax_s2 at location 16 is defined according to the expression (17). This location corresponds the medial part of vagina. This parameter has units of [kPa] and characterizes stress at known tissue displacement (strain) at probe rotation.

$$Pmax\_s2 = \max_{x=medial}\{P_{left\_iside}(x)\} \qquad (17)$$

Test 4: Parameter 27—Displacement of the Anterior Pressure Peak

Displacement of anterior maximum pressure peak along the vaginal canal during Valsalva maneuver dL_a is calculated according to the expression (18). The x-coordinate of anterior pressure peak at rest $x_{max(Pa)\_rest}$ is subtracted from x-coordinate of the pressure peak at Valsalva maneuver $x_{max(Pa)\_Valsalva}$. The x-coordinate is directed along the vaginal canal from hymen to cervix.

$$dL\_a = x_{max(Pa)\_Valsalva} - x_{max(Pa)\_rest} \qquad (18)$$

Test 4: Parameter 30—Displacement of the Posterior Pressure Peak

Displacement of posterior maximum pressure peak along the vaginal canal during Valsalva maneuver dL_p is calculated according to the expression (19). The x-coordinate of posterior pressure peak at rest $x_{max(Pp)\_rest}$ is subtracted from x-coordinate of the pressure peak at Valsalva maneuver $x_{max(Pp)\_Valsalva}$. The x-coordinate is directed along the vaginal canal from hymen to cervix.

$$dL\_p = x_{max(Pp)\_Valsalva} - x_{max(Pp)\_rest} \qquad (19)$$

Test 5: Parameter 34—Posterior Contractive Force

The posterior contractive force dF_p is calculated as a cumulative force increase acting on pressure sensors contacting with the posterior vaginal wall during voluntary pelvic floor muscle contraction according to the expression (20). The pressures at rest Pr are subtracted from the pressures at maximum contraction values Pc.

$$dF\_p = \Sigma_{x=0 \ldots cervix}(Pc_{posterior}(x) \times A_{posterior}(x)) - \Sigma_{x=0 \ldots cervix}(Pr_{posterior}(x) \times A_{posterior}(x)) \qquad (20)$$

Test 5: Parameter 36—Maximum Posterior Contractive Pressure

Maximum posterior contractive pressure Pmax_p during voluntary pelvic muscle contraction is calculated according to the expression (21).

$$Pmax\_p = \max_{x=0 \ldots cervix}\{P_{posterior}(x)\} \qquad (21)$$

Test 6: Parameter 38—Maximum Change of Right-Side Pressure

Maximum change of right-side pressure dPmax_r during voluntary pelvic muscle contraction is calculated according to the expression (22). The pressure at rest Pr is subtracted from the pressure at maximum contraction values Pc.

$$dPmax\_r = \max_{x=0 \ldots cervix}\{Pc_{right\text{-}side}(x) - Pr_{right\text{-}side}(x)\} \qquad (22)$$

Test 6: Parameter 39—Maximum Right-Side Contractive Pressure

Maximum right-side contractive pressure Pmax_r during voluntary pelvic muscle contraction is calculated according to the expression (23).

$$Pmax\_r = \max_{x=0 \ldots cervix}\{P_{right\text{-}side}(x)\} \qquad (23)$$

Test 6: Parameter 41—Maximum Change of Left-Side Pressure

Maximum change of left-side pressure dPmax_l during voluntary pelvic muscle contraction is calculated according to the expression (24). The pressure at rest Pr is subtracted from the pressure at maximum contraction values Pc.

$$dPmax\_l = \max_{x=0 \ldots cervix}\{Pc_{left\text{-}side}(x) - Pr_{left\text{-}side}(x)\} \qquad (24)$$

Test 6: Parameter 42—Maximum Left-Side Contractive Pressure

Maximum left-side contractive pressure Pmax_l during voluntary pelvic muscle contraction is calculated according to the expression (25).

$$Pmax\_l = \max_{x=0 \ldots cervix}\{P_{left\text{-}side}(x)\} \qquad (25)$$

Test 7: Parameter 44—Anterior Peak Pressure Decline

Anterior peak pressure decline dpcdt_a during involuntary pelvic muscle relaxation is calculated according to the expression (26). The pressure decline $P_{anterior}(x,t_o+3)$ is taken after 3 seconds from the maximum muscle contractive pressure $Pc_{anterior}(x,t_o)$ at $t_o$.

$$dpcdt\_a = -100\% \times \{\max_{x=0 \ldots cervix}(Pc_{anterior}(x,t_o)) - P_{anterior}(x,t_o+3)\} / \max_{x=0 \ldots cervix}(Pc_{anterior}(x,t_o)) \qquad (26)$$

Test 7: Parameter 46—Posterior Peak Pressure Decline

Posterior peak pressure decline dpcdt_p during involuntary pelvic muscle relaxation is calculated according to the expression (27). In this test, a patient is asked to squeeze the pelvic muscles and keep it. The involuntary pressure decline $P_{posterior}(x,t_o+3)$ is taken after 3 seconds from the maximum muscle contractive pressure $Pc_{posterior}(x,t_o)$ at $t_o$.

$$dpcdt\_p = -100\% \times \{\max_{x=0 \ldots cervix}(Pc_{posterior}(x,t_o)) - P_{posterior}(x,t_o+3)\} / \max_{x=0 \ldots cervix}(Pc_{posterior}(x,t_o)) \qquad (27)$$

Test 8: Parameter 48—Maximum Change of Anterior Pressure

Maximum change of anterior pressure dPmax_a during reflex pelvic muscle contraction is calculated according to the expression (28). The pressure at rest Pr is subtracted from the pressure at maximum contraction values Pc.

$$dPmax\_a = \max_{x=0 \ldots cervix}\{Pc_{anterior}(x) - Pr_{anterior}(x)\} \qquad (28)$$

Test 8: Parameter 49—Displacement of the Anterior Pressure Peak

Displacement of anterior maximum pressure peak along the vaginal canal during reflex muscle contraction (cough) dL_a is calculated according to the expression (29). The x-coordinate of anterior pressure peak at rest $x_{max(pa)\_rest}$ is subtracted from the x-coordinate of the pressure peak at reflex contraction $x_{max(Pa)\_reflex}$. The x-coordinate is directed along the vaginal canal from hymen to cervix.

$$dL\_a = x_{max(Pa)\_reflex} - x_{max(Pa)\_rest} \qquad (29)$$

Test 8: Parameter 51—Maximum Change of Posterior Pressure

Maximum change of posterior pressure dPmax_p during reflex pelvic muscle contraction is calculated according to the expression (30). The pressure at rest Pr is subtracted from the pressure at maximum contraction values Pc.

$$dP\max\_p = \max_{x=0 \ldots cervix}\{Pc_{posterior}(x) - Pr_{posterior}(x)\} \quad (30)$$

Biomechanical Integrity Score

Figure 5:
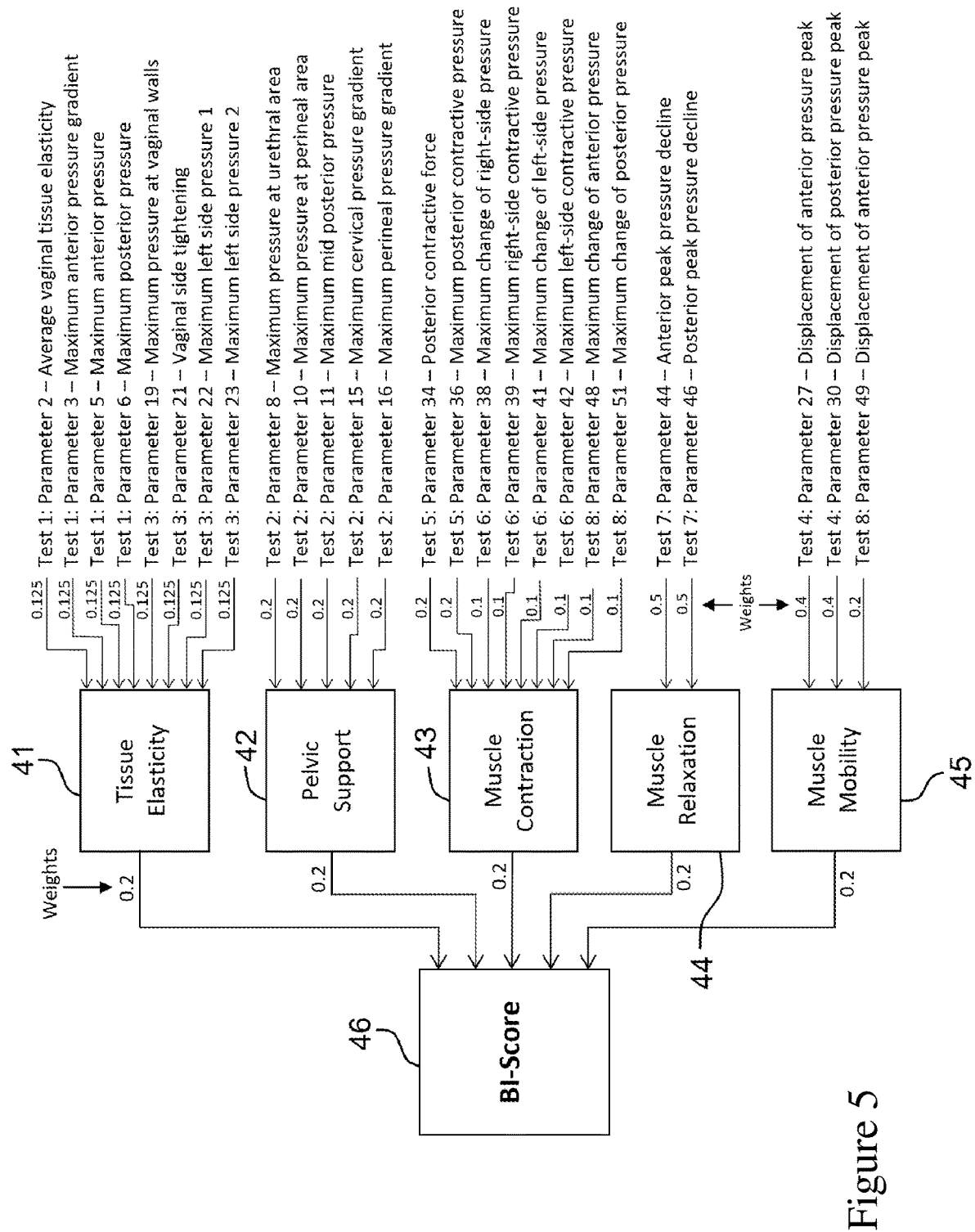
FIG. 5 is a diagram illustrating the composition of the Biomechanical Integrity Score from five components and VII parameters contributing to these components with specific weights.

FIG. 5 shows how a Biomechanical Integrity Score may be determined. At first, the 26 selected parameters are subdivided into five groups in order to characterize the following:
   a. tissue elasticity 41,
   b. pelvic support 42,
   c. pelvic muscle contraction 43,
   d. muscle relaxation 44, and muscle mobility 45 (see FIG. 5).

Component 41 comprises eight parameters with equal weights of 0.125 (the total of all weights for each component must be equal to 1.0), component 42 comprises five parameters with equal weights of 0.2, component 43 consists of eight parameters with weights of 0.1 and 0.2, component 44 comprises two parameters with the weight of 0.5, and component 45 consists of three parameters with the weight of 0.2 and 0.4. Finally, these five components create the Biomechanical Integrity score 46 with equal weights of 0.2 as shown in FIG. 5. Initially, most of the weights may be selected to be equal in each group so that their respective sum equates to 1.0 for each category. In some cases, the relative weight of each component may be reduced or increased if it is determined that this particular component has a respectively low or high influence on the overall result.

The Biomechanical Integrity Score is the composite score that consists of five components as shown in FIG. 5. It may be determined as a weighted average of these components. The weight for each component and its subcomponents may be predetermined in advance. These five components bring different aspects of biomechanical characterization of the pelvic floor. Due to the exclusion of the highly correlated original VTI parameters with r≥0.85, the mutual correlation coefficients have an average value of r=0.27, which is considered as low or negligible correlated. It is important to note that the tissue elasticity component integrates the tissue/structure elasticity for 0-8 mm layer behind the vaginal walls, from the depth comparative with the vaginal wall deformations in Test 1 and 3 (see FIG. 5 and parameter interpretation in Table 2). The pelvic support component integrates the structure support from a depth of 10-45 mm which is about the same as the vaginal wall deformations in Test 2 (see FIG. 5 and parameter interpretation in Table 2).

Figure 6:
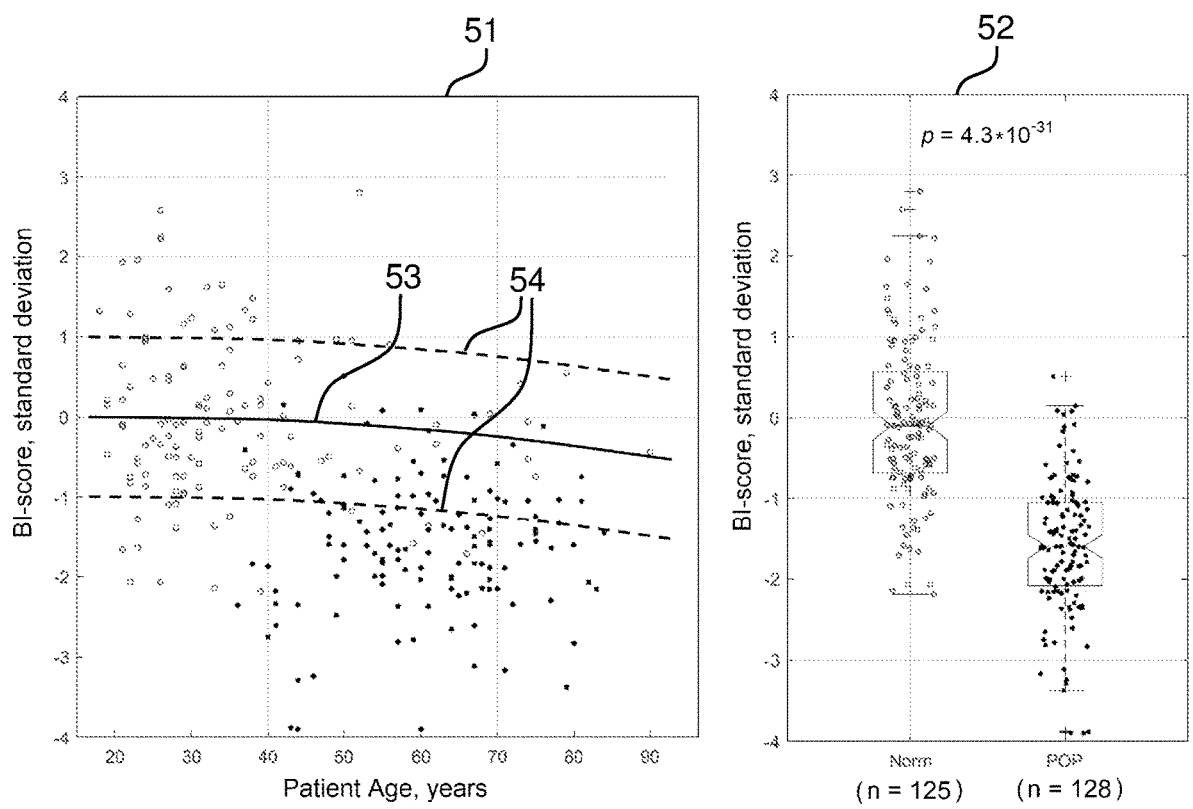
FIG. 6 shows a Biomechanical Integrity Score calculated for normal (empty circles) and POP (black circles) cases against patient age for 253 cases (left panel). Biomechanical Integrity Score boxplots for the same normal and POP cases.

All the Biomechanical Integrity Score data for 253 subjects analyzed here can be visualized on one graph as a function of the subject's age (see panel 51 in FIG. 6). Empty circle dots present the data for women with normal pelvic floor conditions; black-filled circle dots present the data for women with POP conditions. A $2^{nd}$ order polynomial fit for the Biomechanical Integrity Score values against the subject's age for all the 125 subjects in the group with normal pelvic conditions is presented by line 53 (reference line) in FIG. 6. The dashed lines 54 show ±1.0 standard deviation from the reference line. Panel 52 in FIG. 6 shows the same Biomechanical Integrity Score data in two boxplots for normal and POP pelvic conditions. One may observe a significant separation between these two groups; the t-test gives $p=4.3\times10^{-31}$ for these two groups. These results can be considered as statistically significant validation for the Biomechanical Integrity Score sensitivity to POP conditions. Since POP is often associated with concomitant pelvic floor disorders, including urinary and fecal incontinence, pelvic pain, voiding, and sexual dysfunctions, and these disorders are thought to share common pathogeneses, tissue elasticity changes, weakening of the connective support tissues, and pelvic floor muscle dysfunction, the proposed Biomechanical Integrity Score may be used for the characterization of any of the above listed pelvic disorders and/or their combination.

Figure 7:
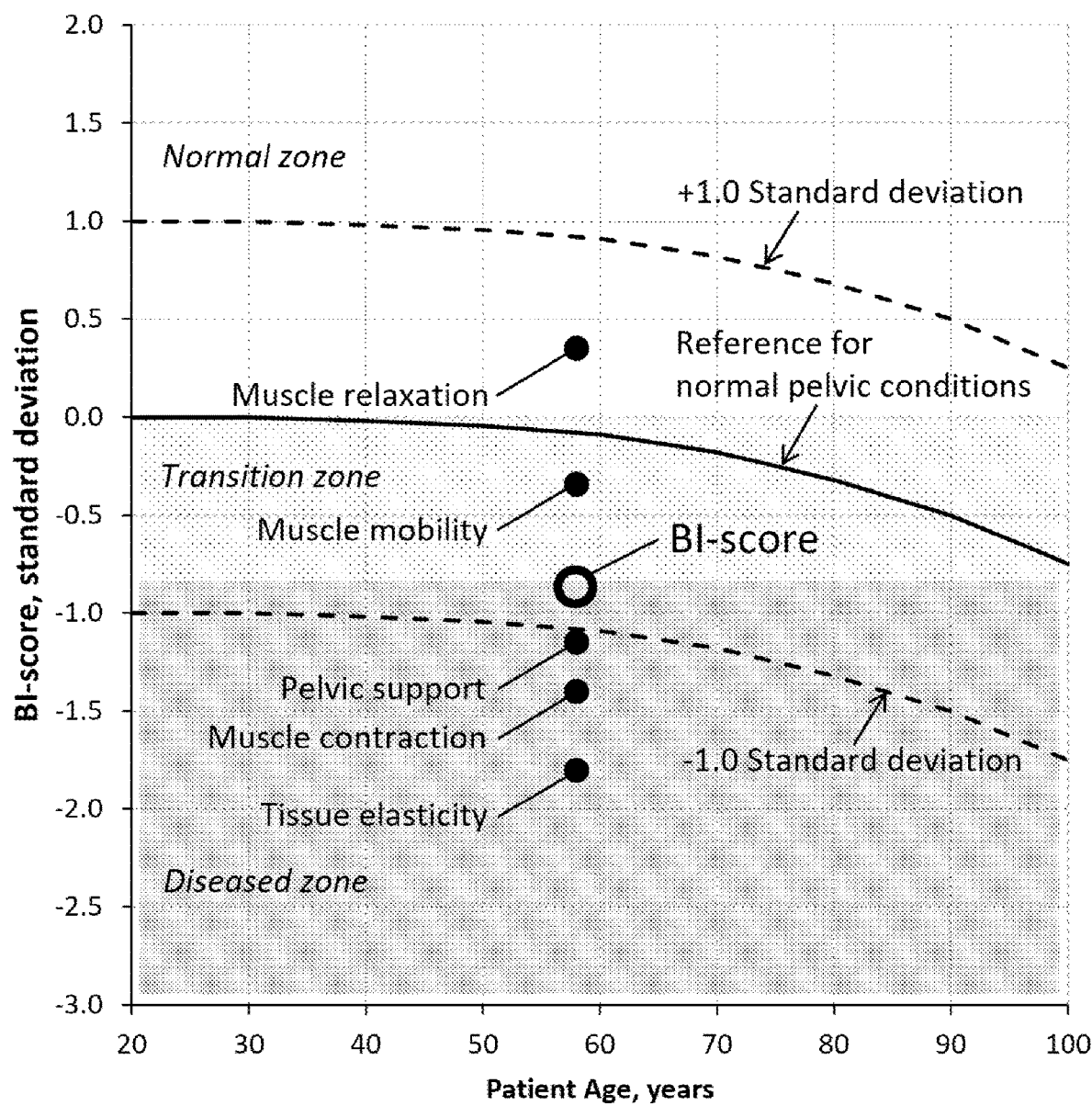
FIG. 7 is an example of examination results with Biomechanical Integrity Score and its five components for 58 y.o. patient with stage 2 anterior prolapse.

FIG. 7 illustrates the Biomechanical Integrity Score and all its five components presented on one graph with the same vertical axis (Standard Deviation) since all of them have the same units. Three backgrounds denote the zones of certainly normal pelvic conditions with Biomechanical Integrity Score above zero (white color, no background), transition with Biomechanical Integrity Score below zero but above −0.8 (bright dotted gray), and diseased zone with Biomechanical Integrity Score below −0.8 (dark gray). The transition from white to bright gray background at Biomechanical Integrity Score=0 has sensitivity=95.3% and specificity=51.2% for the detection of POP conditions. The transition from bright gray to dark gray background at Biomechanical Integrity Score=−0.80 has almost equalized sensitivity=82.8% and specificity=84.0% for diagnosing POP conditions. The POP diagnostic accuracy of the Biomechanical Integrity Score, calculated as an area under a receiver operating characteristics (ROC) curve for the analyzed sample, was found as 89.7%. An age-adjusted Biomechanical Integrity Score can also be calculated relative to the normal curve in FIG. 7.

Figure 8:
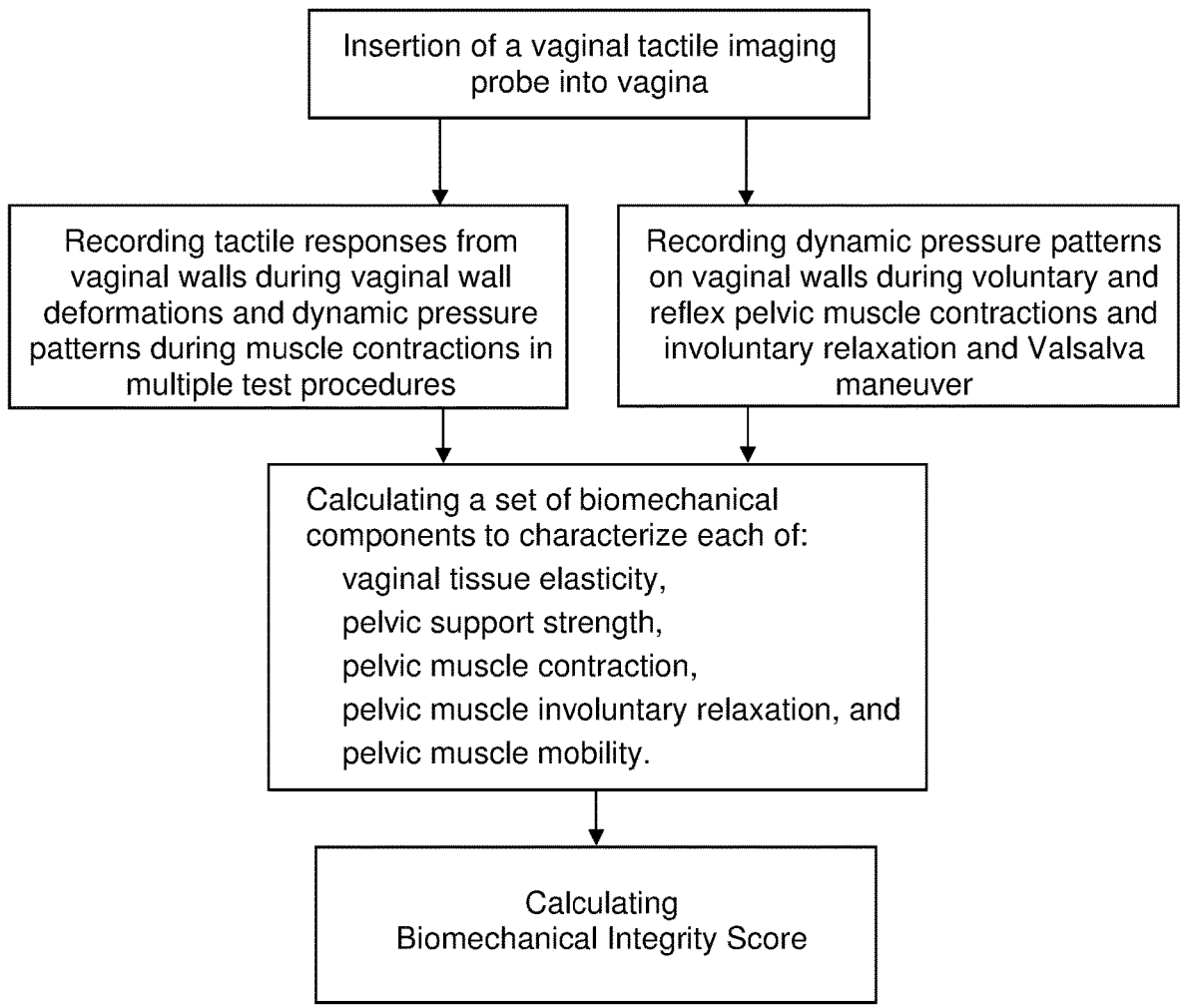
FIG. 8 shows a flow chart illustrating a method for characterization of the female pelvic floor conditions with a biomechanical integrity score.

FIG. 8 illustrates one method for characterization of the female pelvic floor conditions with biomechanical integrity score according to the present invention, the method comprising the steps of:
   a) inserting a vaginal tactile imaging probe into the vagina, the probe equipped with a plurality of tactile sensors distributed along an external surface thereof;
   b) recording tactile response for vaginal walls in contact with the vaginal tactile imaging probe during vaginal wall deformation caused by moving the vaginal tactile imaging probe;
   c) recording dynamic pressure patterns on vaginal walls in contact with the vaginal tactile imaging probe during voluntary and reflex pelvic muscle contractions and involuntary relaxation and Valsalva maneuver and without further movement of the vaginal tactile imaging probe;
   d) using the recorded tactile responses in step (b) and the recorded dynamic pressure patterns in step (c) for calculating a set of biomechanical components to characterize each of:
      vaginal tissue elasticity,
      pelvic support strength,
      pelvic muscle contraction,
      pelvic muscle involuntary relaxation,
      pelvic muscle mobility, and
   e) using the set of biomechanical components calculated in step (d) to calculate a biomechanical integrity score.

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

What is claimed is:

1. A method for determining a biomechanical integrity score to be used for characterization of female pelvic floor conditions, said method comprising the steps of:
   (a) inserting a vaginal tactile imaging probe into vagina, said probe equipped with a plurality of tactile sensors distributed along an external surface thereof;
   (b) recording tactile response from said plurality of tactile sensors while configured to be in contact with vaginal walls during vaginal wall deformation caused by moving said vaginal tactile imaging probe;
   (c) recording dynamic pressure patterns on vaginal walls in contact with said vaginal tactile imaging probe during voluntary and reflex-initiated pelvic muscle contractions, involuntary relaxation, Valsalva maneuver, and without further movement of said vaginal tactile imaging probe, the dynamic pressure pattern is recorded as time-dependent tactile response for said plurality of tactile sensors;
   (d) using said tactile responses recorded in step (b) and said dynamic pressure patterns recorded in step (c) to determine biomechanical parameters characterizing each of:
     i. vaginal tissue elasticity,
     ii. pelvic support strength,
     iii. pelvic muscle contraction,
     iv. pelvic muscle involuntary relaxation,
     v. pelvic muscle mobility, and
   (e) using biomechanical parameters calculated in step (d) to calculate a biomechanical integrity score as a weighted average thereof and in units of standard deviation.

2. The method as in claim 1, wherein said step (b) further comprising moving said vaginal tactile imaging probe with an angle tip along a vagina till its full length to cause vaginal wall deformations, whereby said tactile response recorded along entire vagina is used to calculate biomechanical parameters characterizing vaginal tissue elasticity.

3. The method as in claim 1, wherein said step (b) further comprising rotating said vaginal tactile imaging probe around an axis coming along the vagina to cause vaginal wall deformations, whereby said tactile response recorded along entire vagina is used to calculate biomechanical parameters characterizing vaginal tissue elasticity.

4. The method as in claim 1, wherein said biomechanical parameters characterizing vaginal tissue elasticity in step (d) comprises:

a) average vaginal tissue elasticity measured at said probe insertion to vagina,
b) maximum value of anterior gradient calculated as a change of pressure per anterior wall displacement in orthogonal direction to a vaginal canal measured at said probe insertion to vagina,
c) maximum value of pressure per anterior wall along the vaginal canal measured at said probe insertion to vagina,
d) maximum value of pressure per posterior wall along the vaginal canal measured at said probe insertion to vagina,
e) maximum value of pressure per vaginal wall measured at a probe rotation,
f) vaginal side tightening,
g) maximum value of pressure per left side vaginal wall in perineal part of vagina measured at said probe rotation, and
h) maximum value of pressure per left side at vaginal wall in medial part of vagina measured at said probe rotation.

5. The method as in claim 1, wherein said step (b) further comprising moving said vaginal tactile imaging probe by 15 to 45 mm to cause high vaginal wall deformations, whereby said tactile response recorded during said high vaginal wall deformations is used to calculate biomechanical parameters characterizing pelvic support strength.

6. The method as in claim 1, wherein said biomechanical parameters characterizing pelvic support strength in step (d) comprises:
a) maximum pressure at anterior urethral area,
b) maximum pressure at posterior perineal area,
c) maximum pressure at posterior compartment in a middle third of vagina,
d) maximum pressure gradient at anterior cervical area, and
e) maximum pressure gradient at posterior perineal area.

7. The method as in claim 1, wherein said step (c) further comprising voluntary pelvic muscle contractions, whereby said dynamic pressure patterns recorded during said contractions are used to calculate biomechanical parameter characterizing pelvic muscle contraction capabilities.

8. The method as in claim 1, wherein said biomechanical parameters characterizing pelvic muscle contraction in step (d) comprises:
a) integral contractive force in posterior compartment,
b) maximum contractive pressure in posterior compartment,
c) maximum pressure change in a right side of vagina,
d) maximum contractive pressure in the right side of vagina,
e) maximum pressure change in a left side of vagina,
f) maximum contractive pressure in the left side of vagina,
g) maximum pressure change in anterior compartment, and
h) maximum pressure change in posterior compartment.

9. The method as in claim 1, wherein said biomechanical parameters characterizing pelvic muscle relaxation comprises:
a) anterior relative pressure change per second for maximum pressure at involuntary relaxation, and
b) posterior relative pressure change per second for maximum pressure at involuntary relaxation.

10. The method as in claim 1, wherein said step (c) further comprising performing the Valsalva maneuver and involuntary (reflex) pelvic muscle contraction at patient's cough, whereby said dynamic pressure patterns recorded during said action are used to calculate biomechanical parameter characterizing pelvic muscle mobility.

11. The method as in claim 1, wherein said biomechanical parameters characterizing pelvic muscle relaxation comprises:
a) displacement of a maximum pressure peak in anterior compartment at Valsalva maneuver,
b) displacement of a maximum pressure peak in posterior compartment at Valsalva maneuver, and
c) displacement of a maximum pressure peak in anterior compartment at reflex pelvic muscle contraction.

12. The method as in claim 1, wherein said biomechanical integrity score is compared to its normal value according to patient's age to determine pelvic floor anomalies.

13. The method as in claim 1, wherein said biomechanical integrity score is used to detect at least one of the following diseased conditions of the female pelvic floor: pelvic organ prolapse, urinary incontinence, pelvic pain, and vaginal tissue atrophy.

14. The method as in claim 1, wherein said biomechanical integrity score is used to characterize the female pelvic floor conditions before a treatment.

15. The method as in claim 1, wherein said biomechanical integrity score is used to monitor the female pelvic floor conditions after a treatment.

16. The method as in claim 1, wherein in step (e) the biomechanical parameters calculated in step (d) are first expressed in units of standard deviation before calculating the biomechanical integrity score, wherein each standard deviation for each biomechanical parameter is determined using an individual average value and an individual standard deviation calculated for each biomechanical parameter.

* * * * *